(12) United States Patent
Gumbs et al.

(10) Patent No.: US 8,409,080 B2
(45) Date of Patent: Apr. 2, 2013

(54) REMOTE ENDOSCOPE HANDLE MANIPULATION

(75) Inventors: Andrew A. Gumbs, Brooklyn, NY (US); Luca Milone, Forest Hills, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 237 days.

(21) Appl. No.: 12/866,473

(22) PCT Filed: Feb. 6, 2009

(86) PCT No.: PCT/US2009/000749
§ 371 (c)(1),
(2), (4) Date: Nov. 3, 2010

(87) PCT Pub. No.: WO2009/099633
PCT Pub. Date: Aug. 13, 2009

(65) Prior Publication Data
US 2011/0201886 A1    Aug. 18, 2011

Related U.S. Application Data (60) Provisional application No. 61/026,819, filed on Feb. 7, 2008.

(51) Int. Cl.
*A61B 1/00* (2006.01)
(52) U.S. Cl. ........ 600/146; 600/131; 600/136; 600/118; 600/152; 600/159
(58) Field of Classification Search .................. 600/136, 600/146, 152, 131, 159, 118
See application file for complete search history.

(56) References Cited

U.S. PATENT DOCUMENTS

| | | | | |
|---|---|---|---|---|
| 4,593,679 A | * | 6/1986 | Collins | 600/146 |
| 4,919,112 A | * | 4/1990 | Siegmund | 600/136 |
| 4,941,454 A | | 7/1990 | Wood et al. | |
| 5,347,989 A | * | 9/1994 | Monroe et al. | 600/131 |
| 5,524,180 A | * | 6/1996 | Wang et al. | 600/118 |
| 5,634,466 A | * | 6/1997 | Gruner | 600/459 |
| 5,951,461 A | * | 9/1999 | Nyo et al. | 600/118 |
| 6,004,263 A | * | 12/1999 | Nakaichi et al. | 600/176 |
| 6,059,719 A | * | 5/2000 | Yamamoto et al. | 600/127 |
| 6,371,907 B1 | * | 4/2002 | Hasegawa et al. | 600/146 |
| 6,468,265 B1 | * | 10/2002 | Evans et al. | 606/1 |

(Continued)

FOREIGN PATENT DOCUMENTS

| | | |
|---|---|---|
| EP | 1825801 | 8/2007 |
| JP | 7275222 | 10/1995 |

OTHER PUBLICATIONS

European Search Report dated Jul. 30, 2012, from Counterpart Application No. EP 09 70 7539 (4 pages).

*Primary Examiner* — John P Leubecker
(74) *Attorney, Agent, or Firm* — Stradley Ronon Stevens & Young, LLP (57) ABSTRACT

Systems and methods permit remote endoscope handle manipulation. This can include a control housing configured to removably attach to an endoscope. A manipulator, associated with the housing, can be configured to engage with a control device of the endoscope with the endoscope attached to the housing. An actuator, drivingly coupled with the manipulator, can be configured to move the manipulator to operate the control device with the endoscope attached to the housing.

16 Claims, 5 Drawing Sheets

U.S. PATENT DOCUMENTS

| | | | |
|---|---|---|---|
| 6,569,084 B1* | 5/2003 | Mizuno et al. | 600/102 |
| 6,858,005 B2* | 2/2005 | Ohline et al. | 600/141 |
| 7,008,376 B2* | 3/2006 | Ikeda et al. | 600/152 |
| 7,435,216 B2* | 10/2008 | Kwon et al. | 600/139 |
| 7,578,786 B2* | 8/2009 | Boulais et al. | 600/142 |
| 7,780,593 B2* | 8/2010 | Ueno et al. | 600/146 |
| 7,828,723 B2* | 11/2010 | Ueno et al. | 600/136 |
| 7,850,642 B2* | 12/2010 | Moll et al. | 604/95.04 |
| 7,918,861 B2* | 4/2011 | Brock et al. | 606/130 |
| 8,118,732 B2* | 2/2012 | Banik et al. | 600/117 |
| 2001/0047183 A1 | 11/2001 | Privitera et al. | |
| 2002/0103418 A1 | 8/2002 | Maeda et al. | |
| 2003/0158462 A1 | 8/2003 | Takase | |
| 2003/0187328 A1 | 10/2003 | Seki et al. | |
| 2003/0216617 A1* | 11/2003 | Hirakui et al. | 600/159 |
| 2004/0073083 A1* | 4/2004 | Ikeda et al. | 600/101 |
| 2005/0054899 A1* | 3/2005 | Miyake | 600/152 |
| 2005/0059960 A1 | 3/2005 | Simaan et al. | |
| 2005/0267327 A1* | 12/2005 | Iizuka et al. | 600/106 |
| 2006/0052664 A1* | 3/2006 | Julian et al. | 600/146 |
| 2006/0161043 A1 | 7/2006 | Neumann et al. | |
| 2006/0258955 A1 | 11/2006 | Hoffman et al. | |
| 2007/0167674 A1 | 7/2007 | Toyama | |
| 2007/0232856 A1* | 10/2007 | Ueno et al. | 600/118 |
| 2007/0238927 A1* | 10/2007 | Ueno et al. | 600/145 |
| 2008/0103358 A1* | 5/2008 | Suzuki | 600/106 |
| 2008/0119695 A1* | 5/2008 | Ueno et al. | 600/136 |
| 2008/0214896 A1* | 9/2008 | Krupa et al. | 600/136 |
| 2009/0012365 A1* | 1/2009 | Ueno et al. | 600/146 |

* cited by examiner

REMOTE ENDOSCOPE HANDLE MANIPULATION

CROSS REFERENCE TO RELATED APPLICATIONS

This application is the U.S. National Phase of International Application No. PCT/US2009/000749 filed on Feb. 6, 2009, and claims priority to U.S. Provisional Application No. 61/026,819 filed on Feb. 7, 2008. Each of these applications is incorporated by reference herein, in its entirety and for all purposes.

BACKGROUND

Natural Orifice Transluminal Endoscopic Surgery (NOTES) is a surgical technique in which procedures are performed with an endoscope passed through a natural orifice, such as the mouth, nose, urethra, vagina, or anus, for instance. An endoscope can also be passed though the umbilicus or a single incision, also referred to as Single Port Access (SPA), such as by using a trocar, in some instances. The endoscope can then be passed through an internal incision, such as an incision in the stomach, vagina, bladder, or colon, for instance. By performing NOTES procedures, external incisions or scars can be limited or eliminated altogether.

OVERVIEW

The present inventors have recognized, among other things, that a factor limiting wider implementation of NOTES is that current endoscopic technology generally involves the presence of two to three doctors (surgeons/endoscopists) to perform a procedure. Most endoscopes were designed to perform relatively simple diagnostic tests and procedures, but were not designed to perform more complex surgeries. To reduce the number of personnel involved in endoscopic procedures, one approach would be to design remotely or robotically controlled endoscopes. However, such technology is not presently commercially available. In addition, the potentially high economic costs of such remotely or robotically controlled endoscopes may be a limiting factor in their widespread adoption. In this document, the inventors describe systems and methods for remote endoscope handle manipulation.

In some embodiments, systems for remote endoscope handle manipulation include a control housing configured to removably attach to an endoscope. A manipulator, associated with the housing, is configured to engage with a control device of the endoscope with the endoscope attached to the housing. An actuator, drivingly coupled with the manipulator, is configured to move the manipulator to operate the control device with the endoscope attached to the housing.

In some embodiments, methods of using a remote endoscope handle manipulation system include attaching a control housing to an endoscope. A manipulator of the control housing is engaged with a control device of the endoscope. The manipulator is controlled to operate the control device of the endoscope.

In some embodiments, systems for remote endoscope handle manipulation include means for engaging a control device of an endoscope. The systems include means for remotely controlling the control device of the endoscope.

Example 1 describes an example of a system for remote endoscope manipulation. In this example, the system can comprise a control housing configured to removably attach to an endoscope. A manipulator can be associated with the housing. The manipulator can be configured to engage with a control device of the endoscope with the endoscope attached to the housing. An actuator can be drivingly coupled with the manipulator. The actuator can be configured to move the manipulator to operate the control device with the endoscope attached to the housing.

In Example 2, the system of Example 1 can optionally be configured such that the manipulator includes a rotational manipulator configured to engage with a rotational control device of the endoscope.

In Example 3, the system of any one or more of Examples 1-2 can optionally be configured such that the rotational manipulator includes a stepper motor.

In Example 4, the system of any one or more of Examples 1-3 can optionally be configured such that the rotational control device includes a gear configured to control movement of a shaft of the endoscope.

In Example 5, the system of any one or more of Examples 1-4 can optionally be configured such that the manipulator includes a translational manipulator configured to engage with a translational control device of the endoscope.

In Example 6, the system of any one or more of Examples 1-5 can optionally be configured such that the translational manipulator includes a solenoid.

In Example 7, the system of any one or more of Examples 1-6 can optionally be configured such that the translational manipulator can be configured to control a translational control device that is configured to control irrigation, suction, or insufflation.

In Example 8, the system of any one or more of Examples 1-7 can optionally comprise a controller communicatively coupled to the housing, the controller configured to send a control signal to the actuator to operate the manipulator.

In Example 9, the system of any one or more of Examples 1-8 can optionally be configured such that the controller includes a foot pedal.

In Example 10, the system of any one or more of Examples 1-9 can optionally be configured such that the control housing is configured to removably attach to an endoscope handle.

In Example 11, the system of any one or more of Examples 1-10 can optionally be configured such that the control housing is configured to partially cover a portion of the endoscope.

Example 12 describes an example of a method. In this example, the method comprises attaching a control housing to an endoscope, engaging a manipulator of the control housing with a control device of the endoscope, and controlling the manipulator to operate the control device of the endoscope.

In Example 13, the method of Example 12 can optionally be performed such that controlling the manipulator includes using a foot pedal to control the manipulator.

In Example 14, the method of any one or more of Examples 12-13 can optionally be performed such that controlling the manipulator to operate the control device permits controlling movement of a shaft of the endoscope.

In Example 15, the method of any one or more of Examples 12-14 can optionally be performed such that controlling the manipulator to operate the control device permits controlling irrigation, suction, or insufflation using the endoscope.

In Example 16, the method of any one or more of Examples 12-15 can optionally comprise restraining the housing to inhibit movement of a portion of the endoscope.

In Example 17, the method of any one or more of Examples 12-16 can optionally be performed such that attaching the control housing to an endoscope includes attaching the control housing to an endoscope handle.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

The drawings illustrate generally, by way of example, but not by way of limitation, various embodiments discussed in the present document.

DESCRIPTION

The present inventors have recognized, among other things, that current endoscopic technology involves the presence of two to three doctors (surgeons/endoscopists) to perform a procedure. Robotic endoscopic surgery systems are not yet commercially available, and, if or when such systems become available, the costs of such systems may inhibit wide usage of the systems.

Accordingly, the present inventors have developed systems and methods for remote or robotic endoscope handle manipulation, which, among other things, can reduce the number of doctors involved in an endoscopic procedure to one or two doctors. Moreover, the systems and methods can make use of existing endoscope devices, thereby reducing additional costs associated with the use of the present systems and methods. Additionally, the present systems and methods can be put into practice currently and can be made commercially available in the short term.

In some examples, a system for remote endoscope handle manipulation includes a portion that fits over at least a portion of a handle of an existing endoscope and is configured to manipulate one or more controls on the endoscope handle. In an example, the system includes a controller for a doctor or other operator to use to remotely manipulate the one or more controls on the endoscope handle. In an example, the controller includes a foot pedal to allow the operator to remotely control at least some aspects of the endoscope with a foot, thereby freeing up a hand of the operator, such as to facilitate performing one or more other aspects of the endoscopic procedure.

Figure 2:
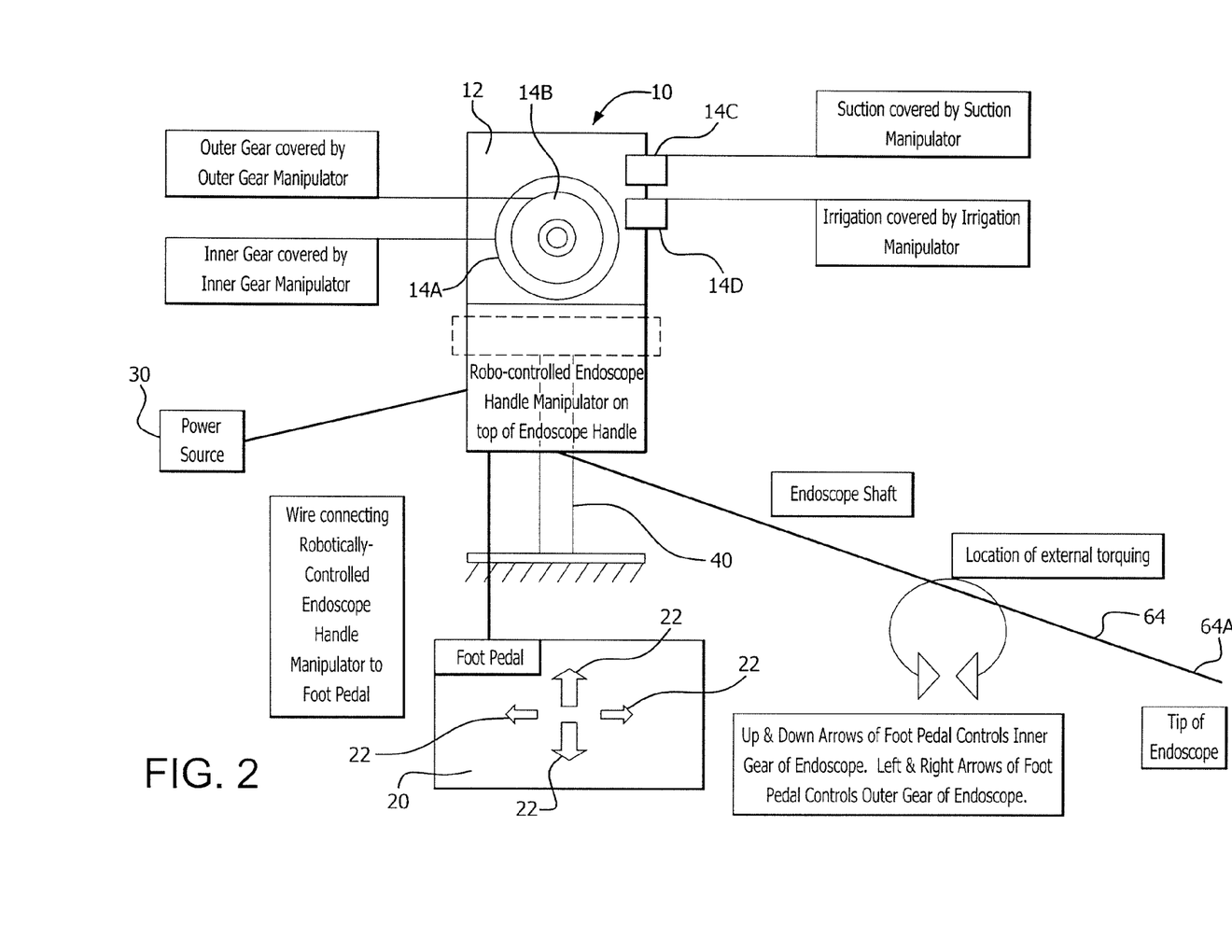
FIG. 2 is a is a diagrammatic representation of a system for remote endoscope handle manipulation according to some embodiments of the disclosed subject matter, the system being attached to an endoscope handle.
Figure 3:
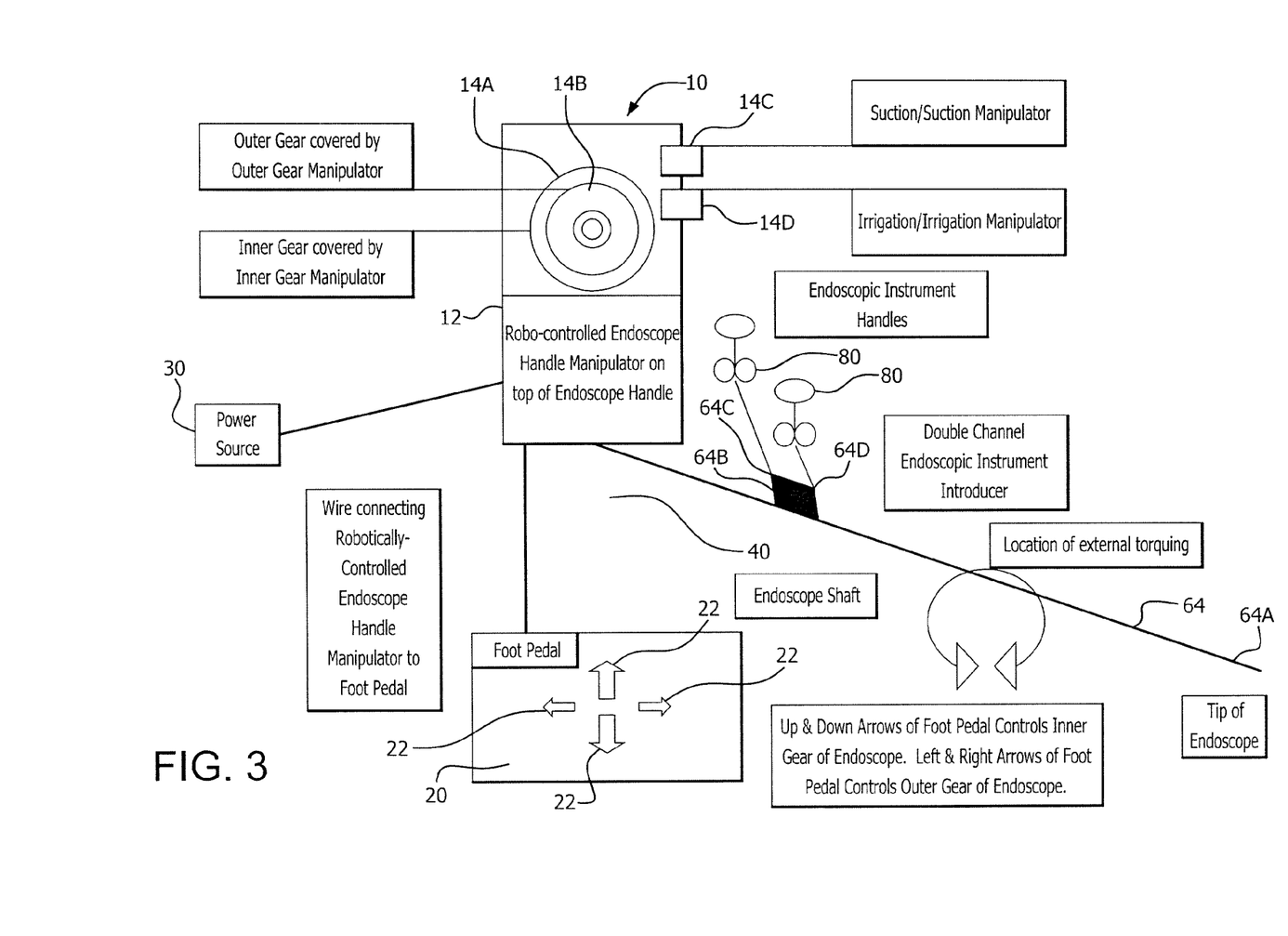
FIG. 3 is a is a diagrammatic representation of a system for remote endoscope handle manipulation according to some embodiments of the disclosed subject matter, the system being attached to an endoscope handle.
Figure 4:
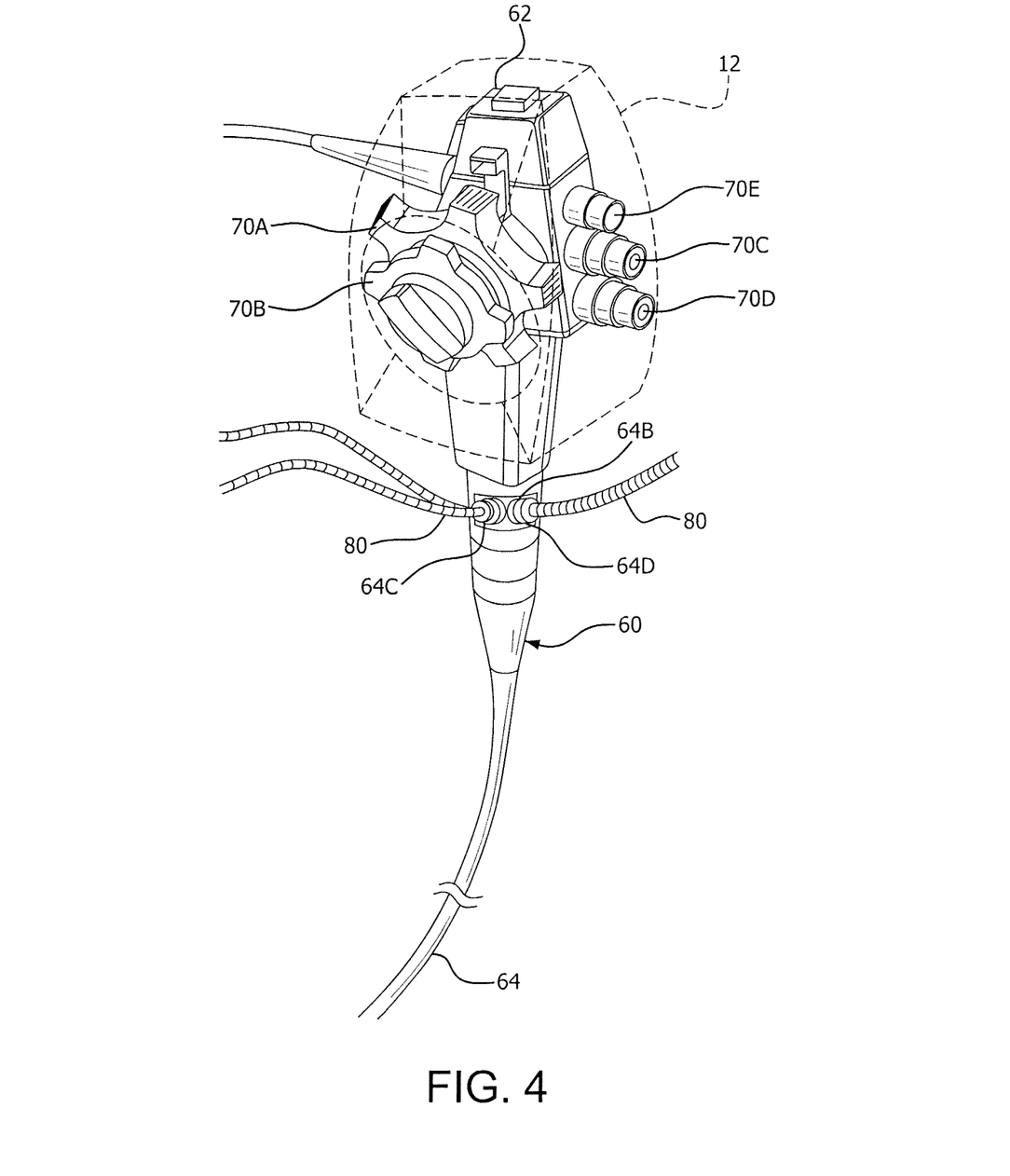
FIG. 4 is a perspective view of a system for remote endoscope handle manipulation according to some embodiments of the disclosed subject matter, the system being attached to an endoscope handle.
Figure 5:
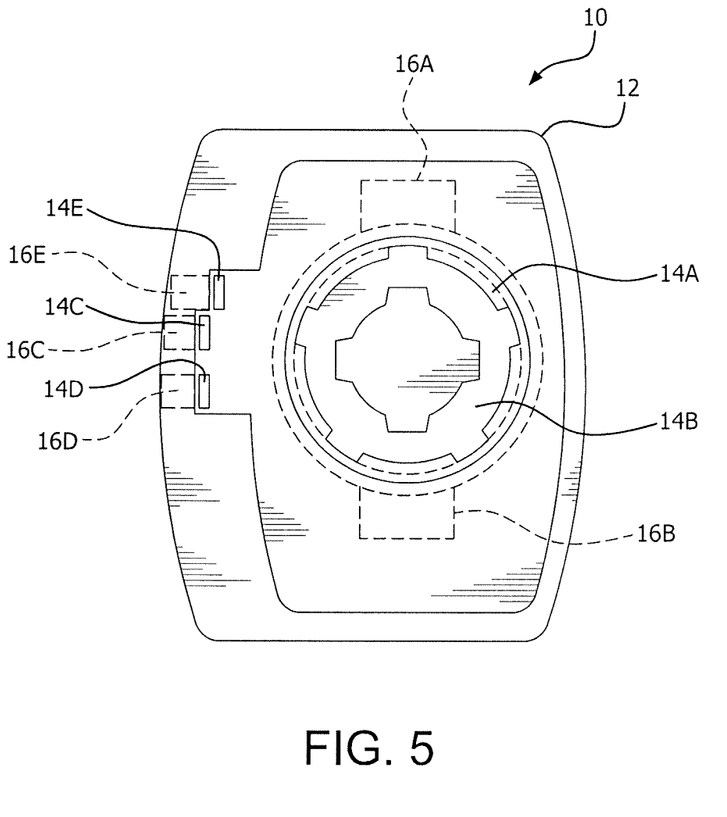
FIG. 5 is an elevational view of an interior portion of a system for remote endoscope handle manipulation according to some embodiments of the disclosed subject matter.

Referring to FIGS. 1-4, in an example, an endoscope 60 includes a shaft 64 and a handle 62 with one or more control devices 70 associated with the handle 62. In an example, the control devices 70 include two gears, such as a first or outer gear 70A and a second or inner gear 70B, that respectively control upward/downward movement and side-to-side movement of a tip 64A of the endoscope shaft 64. The control devices 70 can further include a first button 70C for controlling suction/insufflation and a second button 70D for controlling irrigation. As shown in FIG. 4, the endoscope 60 can further include a third button 70E, which can be used to control another operational aspect of the endoscope 60, such as, for instance, power, camera, light, suction or insufflation (e.g., if suction and insufflation are not controlled with the same control device), or another endoscopic function.

In use, in an example, natural orifice transluminal endoscopic surgeries (NOTES) can be performed by introducing the shaft 64 into a patient's orifice (for instance, the mouth, anus, vagina, or another orifice, or the umbilicus or another incision) and directing the shaft 64 to a desired location within the patient's body, such as by external urging or torquing (FIGS. 2 and 3 depict a possible location along the shaft 64 for such urging or torquing) of the shaft 64 and controlling movements of the tip 64A with the first and second gears 70A, 70B. In an example, as shown in FIGS. 3 and 4, the endoscope 60 includes a port 64C for the introduction of one or more endoscopic devices or tools 80, such as, for instance graspers, endoscopic shears, electrocautery devices, cameras, lights, or other devices or tools. The port 64C can include first and second channels 64C, 64D so that two tools or devices 80 can be inserted into the shaft 64 at the same time. However, the port 64C can include more than or fewer than two channels.

Figure 1:
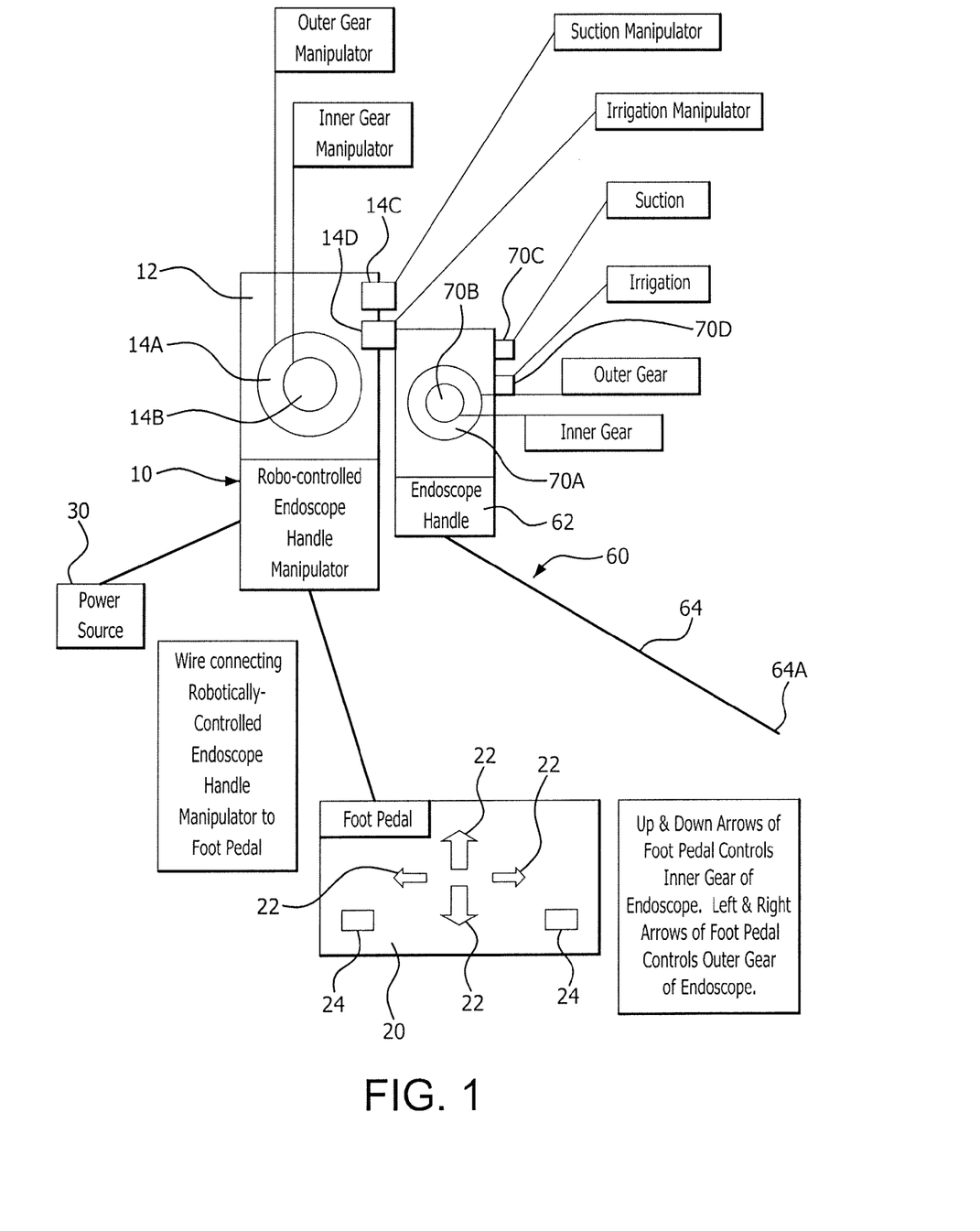
FIG. 1 is a diagrammatic representation of a system for remote endoscope handle manipulation according to some embodiments of the disclosed subject matter, the system being removed from an endoscope handle.

In some examples, the systems 10 attach to an existing flexible endoscope 60 to allow for the first and second gears 70A, 70B of the endoscope 60 to be controlled remotely with a controller 20. In an example, the controller 20 includes a foot pedal interface 20. This can liberate the activity of one operator hand and enable two and possibly even one operator to perform NOTES surgery. In an example, the controller 20 includes one or more controls 22 such as buttons, pedals, or switches, for instance, which allow the operator to actuate one or more of the controls 22, for instance, with a foot, to control aspects of the endoscope 60. As shown in FIGS. 1-3, the controls 22 can include four arrow buttons, which can control movement of the tip 64A of the endoscope shaft 64. Other controls can be included on the controller 20, such as to control one or more other aspects of the endoscope 60, such as suction, insufflation, irrigation, or operation of one or more endoscopic tools or devices used with the endoscope 60.

In an example, the system 10 includes or is coupled to an electrical or other power source 30 to power one or more components of the system 10. The power source 30 can include a plug or other connector for attaching to an external source of power, such as a wall outlet or a generator, or can include one or more batteries.

In some examples, the systems 10 can include a cradle or holder 40 (FIG. 2) for holding or otherwise restraining movement of the endoscope handle 62. In an example, the handle 62 or other portion of the endoscope 60 or system 10 can be affixed or otherwise attached to or rested upon a portion of the holder 40. Another portion of the holder 40 can then be affixed or otherwise attached to or placed on a table, stand, or other surface. For instance, the holder 40 can include legs or a base for placement on a table, or the holder can include a clamp for fixed attachment to a table. In an example, the holder 40 can be used to hold the endoscope 60 or system 10 during use, for instance, at a particular orientation, so that an operator need not hold the endoscope 60 or system 10. Use of the holder 40 helps further liberate one or more hands of one or more operators, such as to allow an operator to perform one or more other activities.

In some examples, the systems 10 can be configured to fit one or most standard flexible endoscope handles. For instance, currently, a majority of endoscopes are made by two companies, Olympus and Storz, with both companies making endoscopes with inner and outer overlapping gear controls and separate buttons for suction and irrigation control, such as shown in FIGS. 1 and 4.

Referring to FIGS. 1-4, in an example, the system 10 includes a housing 12 that is sized and shaped to fit over at least a portion of the endoscope handle 62. FIG. 4 shows an example in which the housing 12 (shown in phantom) is placed over a portion of the handle 62 to control of or otherwise interact with the control devices 70A, 70B, 70C, 70D, 70E of the endoscope 60. The housing 12 can be attached to the endoscope handle 62, for instance, by forming a shell around all or a portion of the handle 62; using one or more straps, clamps, or other attachment devices; using a detent configuration to snap onto the handle 62; or using frictional engagement between the handle 62 and the housing 12. Although shown in FIG. 4 as generally surrounding the handle 62, in some examples, the housing can be a frame or any other structure, including one or more straps, tape, or adhesive, for instance, that can be attached to the handle 62 or other portion of the endoscope 60 to position one or more manipulators, as described below, to allow control of or interaction with the control devices of the endoscope 60.

Referring to FIGS. 1-5, in an example, the housing 12 includes one or more manipulators 14, which are positioned such that they will align with a respective one or more of the control devices 70 of the endoscope 60 when the housing 12 is attached to the handle 62. For instance, a first gear manipulator 14A can be configured to be complementarily shaped and sized to engage with the first gear 70A of the endoscope handle 62, such that rotation of the first gear manipulator 14A causes rotation of the first gear 70A of the endoscope handle 62. In an example, a second gear manipulator 14B can be complementarily shaped and sized to engage with the second gear 70B of the endoscope handle 62, such that rotation of the second gear manipulator 14B causes rotation of the second gear 70B of the endoscope handle 62. In an example, the first and second gear manipulators 14A, 14B are drivingly coupled to first and second actuators 16A, 16B, respectively. For instance, an outer edge of each of the first and second gear manipulators 14A, 14B can include gear teeth, which can be engaged by a worm or pinion driven by one of the first and second actuators 16A, 16B. In an example, the first or second actuators 16A, 16B can include a rotational actuator, such as a stepper motor, for instance. The first or second actuators 16A, 16B can be independently controlled, such as by actuating different controls 22 on the controller 20, thereby allowing the operator to individually control different aspects of the endoscope 60 using the controller 20.

Still referring to FIGS. 1-5, in some examples, the systems 10 can include one or more translational manipulators, which align with translational control devices, such as buttons, sliders, or switches, of the endoscope handle 62, with the housing 12 attached to the endoscope handle 62. In an example, the housing includes first, second, and third button manipulators 14C, 14D, 14E, which are configured to align with the first, second, and third buttons 70C, 70D, 70E, such that translation of the first, second, or third button manipulator 14C, 14D, 14E causes translation of the first, second, or third button 70C, 70D, 70E of the endoscope handle 62. In an example, each of the first, second, and third button manipulators 14C, 14D, 14E provides a surface coupled to a driven portion of a translational actuator, such as a solenoid, for instance. In an example, the first button manipulator 14C is coupled to a third actuator 16C, the second button manipulator 14D is coupled to a fourth actuator 16D, and the third button manipulator 14E is coupled to a fifth actuator 16E. The third, fourth, and fifth actuators 16C, 16D, 16E can be independently controlled such as by respective actuating controls 24 (FIG. 1) on the controller 20. This allows the operator to remotely control one or more aspects of the endoscope 60 using the controller 20, without requiring the operator to manipulate controls at the endoscope handle. The number of manipulators and actuators can be increased or decreased, such as to correspond to the number of translational controls on the endoscope. For example, the housing need not include any translational actuators if manual actuation of the translational controls of the endoscope is desired. In this instance, for example, the housing can include an opening therein to allow operator access to one or more of the buttons 70C, 70D, 70E, or can include one or more manipulators that, rather than being coupled to respective actuators, are instead manually operated by the operator from outside of the housing 12.

Although the controller 20 is described above as electrically communicating with actuators to manipulate the control devices 70 of the endoscope 60, in some examples, the controller can mechanically communicate with the manipulators, such as by using rotating shafts or translating wires or shafts to mechanically deliver drive power from the controller to the manipulators. The shafts or wires can be rotated or translated using actuators, such as stepper motors or solenoids, for instance, associated with the controller.

Once the system 10 is placed over the endoscope handle 62, the system 10 and endoscope handle 62 can be placed in the cradle or holder 40 and the endoscope tip 64A can be robotically-controlled via one or more commands from the controller 20, such as the foot pedal 20. In another example, the holder or a holding portion is integrated with the control housing or the endoscope (for instance, the endoscope handle), rather than being a separate component. This allows one operator to torque the endoscope shaft 64, as desired, with one hand and to control the one or more endoscopic instruments 80 that are passed through one or more of the channels 64C, 64D with the other hand, thus, permitting a single operator to perform a NOTES procedure or SPA surgery. The present inventors believe that such a system can be cheaper than a fully robotic NOTES endoscope because hospitals can use existing endoscopes with the present systems and methods instead of having to invest in new robotic NOTES endoscopes should they become available on the market.

In other examples, the systems can include one or more attachments that can control one or more of the endoscopic instruments 80 passed through one or more of the channels 64C, 64D. In an example, the system includes a device to remotely control the torquing of the endoscopic shaft 64. For instance, one or more actuators can be attached to the endoscopic shaft 64 to urge the shaft in one or more directions, including an axial direction, a rotational direction, and a radial direction. In an example employing the above-described system 10 together with endoscopic instrument control and endoscopic shaft torque control, an existing endoscope can be totally remotely or robotically controlled.

In some examples, methods of using the remote endoscope handle manipulation system 10 include attaching the control housing 12 to the handle 12 of the endoscope 60, such that at least one manipulator 14A, 14B, 14C, 14D, or 14E of the control housing 12 engages a corresponding control device 70A, 70B, 70C, 70D, or 70E of the endoscope handle 62. The operator can remotely control at least one manipulator 14A, 14B, 14C, 14D, or 14E to remotely operate at least one control device 70A, 70B, 70C, 70D, or 70E of the endoscope handle 62. In one example, the operator uses a controller 20 to operate at least one control device 70A, 70B, 70C, 70D, or 70E of the endoscope handle 62. In an example, the controller 20 includes a foot pedal 20 to allow the operator to operate one or more aspects of the endoscope 60 by foot, thereby freeing up use of an arm or hand of the operator. In an example, the operator can restrain at least a portion of the system 10, such as to inhibit movement of the endoscope handle 62. In an example, the system 10 can be restrained using the holder 40, such as described above. In this way, the operator can free-up use of a hand to allow the operator to control one or more additional endoscope operations, thereby potentially decreasing the number of operators required to perform a NOTES or other endoscopic procedure.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system for remote endoscope manipulation, the system comprising:

an endoscope including a shaft having a tip and a handle having gears for moving the tip in an upward, downward, and side-to-side direction and having one or more buttons for operating an operational aspect of the endoscope including irrigation, suction, insufflation, power, a camera, a light, or a combination thereof;

a control housing removably attached to the endoscope handle;

one or more rotational manipulators on the housing configured to engage the gears, and one or more button manipulators on the housing configured to engage the one or more buttons when the housing is attached to the endoscope handle;

one or more rotational actuators drivingly coupled to the one or more rotational manipulators such that actuation of said one or more rotational actuators rotates the one or more rotational manipulators and rotation of the one or more rotational manipulators rotates the gears, and one or more translational actuators drivingly coupled to the one or more button manipulators such that actuation of said one or more translational actuators translates the one or more button manipulators and translation of the one or more button manipulators translates the one or more buttons, thereby operating an operational aspect of the endoscope;

and a controller communicatively coupled to the housing and configured to communicate with and cause actuation of the one or more rotational actuators and the one or more translational actuators and thereby rotate the gears and operate an operational aspect of the endoscope, the controller including a foot pedal that allows an operator of the system to remotely rotate the gears and operate an operational aspect of the endoscope by foot.

2. The system of claim 1, wherein the one or more rotational actuators drivingly coupled to the one or more rotational manipulators include a stepper motor.

3. The system of claim 1, wherein the one or more translational actuators drivingly coupled to the one or more button manipulators include a solenoid.

4. The system of claim 1, wherein the control housing is configured to partially cover a portion of the endoscope.

5. The system of claim 1, further comprising a holder for holding or restraining movement of the endoscope handle.

6. The system of claim 5, wherein the holder is integral with the control housing.

7. The system of claim 1, wherein the endoscope further includes a port for one or more of a grasper, endoscopic shears, electrocautery device, camera, or light.

8. The system of claim 7, wherein the port comprises two channels.

9. The system of claim 1, wherein the system further comprises a power source.

10. The system of claim 1, wherein the one or more rotational manipulators include gear teeth.

11. The system of claim 1, wherein the controller electronically communicates with and causes actuation of the one or more rotational actuators and the one or more translational actuators.

12. The system of claim 1, wherein the controller mechanically communicates with and causes actuation of the one or more rotational actuators and the one or more translational actuators.

13. The system of claim 1, wherein the foot pedal includes arrow buttons for controlling the direction of movement of the endoscope tip.

14. A method comprising:
attaching a control housing to the handle of an endoscope, the handle including gears for moving a tip of the endoscope in an upward, downward, and side-to-side direction and including one or more buttons for operating an operational aspect of the endoscope including irrigation, suction, insufflation, power, a camera, a light, or a combination thereof, and by using a foot pedal on a controller communicatively coupled to the control housing, rotating the gears by communicating with one or more actuators to rotate one or more rotational manipulators such that rotation of the one or more rotational manipulators rotates the gears, and operating an operational aspect of the endoscope by communicating with one or more translational actuators to translate one or more button manipulators such that translation of the one or more button manipulators translates the one or more buttons, thereby operating an operational aspect of the endoscope.

15. The method of claim 14, wherein the operational aspect is irrigation, suction, or insufflation.

16. The method of claim 14, further comprising restraining the control housing to inhibit movement of a portion of the endoscope.

* * * * *